United States Patent
Kalkum et al.

(12) 
(10) Patent No.: US 6,467,328 B1
(45) Date of Patent: Oct. 22, 2002

(54) PROCESS AND DEVICE FOR DETECTING MICROPARTICLE MOVEMENT

(75) Inventors: Markus Kalkum, New York, NY (US); Markus Kietzmann, Wolfratshausen (DE); Martin Müller, Berlin (DE)

(73) Assignee: Max-Planck-Gesellschaft zur Forderung der Wissenschaften e.V. (DE)

( * ) Notice: Subject to any disclaimer, the term of this patent is extended or adjusted under 35 U.S.C. 154(b) by 0 days.

(21) Appl. No.: 09/555,068

(22) PCT Filed: Nov. 23, 1998

(86) PCT No.: PCT/EP98/07558

§ 371 (c)(1), (2), (4) Date: Jul. 24, 2000

(87) PCT Pub. No.: WO99/27372

PCT Pub. Date: Jun. 3, 1999

(30) Foreign Application Priority Data

Nov. 24, 1997 (DE) .......................... 197 52 010

(51) Int. Cl.⁷ ................................................ G01N 1/00
(52) U.S. Cl. ........................................................ 73/1.01
(58) Field of Search ................. 73/1.01, 1.79, 73/1.81, 865.5, 488; 356/614, 27, 28; 324/178; 222/32, 41

(56) References Cited

U.S. PATENT DOCUMENTS 5,508,200 A 4/1996 Tiffany et al.

FOREIGN PATENT DOCUMENTS

| CH | 668 130 A5 | 11/1988 |
| EP | 0 601 213 | 10/1992 |
| EP | 0 775 587 A1 | 4/1996 |

OTHER PUBLICATIONS

Patent Abstracts of Japan—Detecting Device for Speed of Ink Particles in Ink Jet—Jan. 31, 1981, vol. 5/No. 17.

Analytical Chemistry, vol. 69, Feb. 15, 1997—Characterization of an Inkjet Chemical Microdispenser for Combinatorial Library Synthesis.

*Primary Examiner*—Robert Raevis
(74) *Attorney, Agent, or Firm*—Cook, Alex, McFarron, Manzo, Cummings & Mehler, Ltd.

(57) ABSTRACT

For the detection of the position and/or velocity of microparticles which move from dispensers of a dispensing head (30) to a target, a detector target with two linear bound, electro-acoustic or electro-optic interactive areas which fix a target plane is used. When microparticles impact on the interactive areas, detector signals are determined from which along with the dispensing head position motion parameters of the microparticles are obtained.

9 Claims, 6 Drawing Sheets

PROCESS AND DEVICE FOR DETECTING MICROPARTICLE MOVEMENT

The invention relates to a procedure for detecting the motion properties of microparticles being fired by a microdispenser unit onto a target, in particular to a procedure for detecting the impact points and velocities of microparticles, and a position calibration procedure for a microdispenser unit with a plurality of individual microdispensers. The invention also relates to devices for implementing the procedure, and a device for microparticle detection.

It is generally known to place the smallest substance or solution quantities on a substrate in the form of small, solid particles or droplets (microparticles) using a microdispenser device. The microdispenser device enables the targeted pipetting of specific volumes and positioning on appropriately determined location coordinates. To sequentially place various substances, a microdispenser device usually has a dispensing head with several dispensers, which are set up to position the respective substances. The target positions of the dispensed particles must be precisely known to be able to position the substances in the precise location, e.g., for reaction purposes or to generate defined microsubstance patterns.

Figure 8:
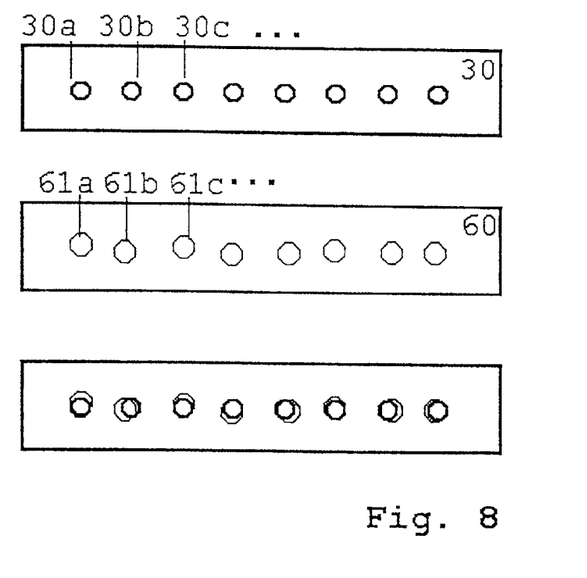

The position of a dispensing head relative to a target substrate can usually be manipulated by means of an adjustment device, with which specific head positions can be set. When the individual dispensers of the dispensing head are fixed in place, they have defined reference positions, which arise from the head position and relative arrangement of the respective dispenser relative to a reference dispenser. The practical application of dispensing heads shows that, at given reference positions of the dispenser, impact points are formed on the substrate target whose relative coordinates do not correspond to the relative coordinates of the dispensers. FIG. 8 explains this diagrammatically based on a dispenser series 30. The individual dispensers 30a, 30b, 30c, . . . are arranged in a straight row. These can be micropipettes or the like, from which microdrops are shot onto a substrate 60. The impact points 61a, 61b, 61c are no longer arranged in a straight row due to minimal misalignments of the dispensers or mechanical instabilities, as can be discerned particularly well in the bottom portion of FIG. 8 from the superposition of dispenser positions and impact points. This behavior is problematical particularly in those cases where a first substance is fired at the substrate from a first dispenser, and a second substance is to be fired from a second dispenser at precisely the same substrate position as the first substance after subsequent movement by the dispenser head. To this end, the adjustment device of the dispensing head needs information about the corresponding dispensing head positions relative to the impact point to go along with the relative dispenser positions.

As is generally known, optical systems have thus far been used to determine the impact points or target positions of dispensed liquids. For example, in a stroboscopic procedure (A. Schober et al. in "BioTechniques", Vol. 15, 1993, p. 324 ff), the drop outline is determined with a first camera, and the target position of the respective drop to be observed is determined with a second camera. As an alternative, a substance pattern generated on a substrate can be optically analyzed. A disadvantage of these detection systems in addition to the high equipment-related outlay involved is that technically complex image recognition processes would be required for automation purposes. This results in a high cost intensity for conventional systems, along with a high susceptibility to errors given their complexity. Due to the resultant unreliability, conventional microdispensing systems have had a narrow range of application in combinatorial chemistry, despite the high technological potential for use in processing highly parallel analytical tasks.

Problems in detecting the motion of dispensed particles are encountered not only in the "drop-on-demand" technique illustrated above, but generally in all microparticle placement or shooting devices with which microparticles are to be deposited on specific positions in a target range along predetermined paths.

The object of the invention is to provide an improved procedure for detecting the motion properties of microparticles, in particular of their impact points and/or velocities on target substrates, which is highly reliable and easy to implement. The object of the invention is also to provide a device for implementing such a procedure, in particular an improved microparticle detector device.

The object of the invention is achieved with a procedure and device with the features described in claims 1, 6 and 10. Advantageous embodiments of the invention derive from the subclaims.

According to the invention, the impact points of the microparticles, the relative coordinates of the impact points and/or their deviation from the relative coordinates of the dispenser positions are detected with a particle detector device, which exhibits two linear-bound interactive areas defining a target plane, and is adapted to emit a detector signal as soon as a microparticle enters one of the interactive areas. In a procedure according to the invention, a dispensing head with numerous dispensers, of which one dispenser emits a sequence of microparticles as a reference dispenser, is first moved along two straight, parallel paths over the detector device in such a way that the rows of drops formed by the microparticle sequence impact said interactive areas at four reference impact points. The dispensing head coordinates respectively set with the adjustment device are determined at the reference impact points as reference dispenser coordinates. In a measuring step, the dispensing head is then moved over the detector device along a measuring path that matches one of the calibration paths or runs parallel to one of them, so that one of the remaining dispensers (measuring dispensers) emits a sequence of microparticles when one of the interactive areas is reached. As soon as a microparticle from a measuring dispenser impacts an interactive area, the measuring dispenser position relative to the position of the dispensing head is determined, and the impact point on the interactive area is ascertained from that. Finally, the distance between the relative coordinates of the microparticle impact point from the measuring dispenser and the corresponding measuring dispenser position yields the sought deviation between the arrangement of the impact point of the microparticle from the measuring dispenser relative to the reference dispenser impact point on the one hand, and the arrangement of the measuring dispenser relative to the reference dispenser on the other.

According to a preferred configuration of the invention, the determined relative deviation coordinates are used to generate a control signal for the adjustment device of the dispensing head to correct the positioning of a dispenser relative to a specific substrate location, always as a function of the expected impact point from the dispenser in question.

Depending on the interactive area layout, the microparticle velocity can also be ascertained in addition to the aforementioned motion parameters.

Viewed from a first aspect, a device according to the invention is formed by the mentioned detector device with two linear bound interactive areas that fix a target plane.

Depending on the underlying measuring principle, the detector device is designed as an electro-acoustic sensor or electro-optic sensor. In the case of an electro-acoustic sensor, each of the interactive areas not parallel to each other is formed by an oscillating element with at least one straight boundary, wherein, when this boundary is reached by one microparticle out of the sequences of microparticles formed along the cited paths, a mechanical oscillation is triggered in the oscillating element. A sound converter is used to convert the mechanical oscillation into a detector signal, which, after suitable signal processing, indicates the interactive area that was hit by a microparticle. The oscillating element preferably is shaped like a tensioned elastic thread connected with a membrane of a microphone that acts as the sound converter. In this case, the detector device has two straight, fixed threads aligned at a predetermined angle (≠0), preferably made out of metal, which fix the target plane and are each connected with a microphone. When designed as an electro-optic sensor, each interactive area is formed by a straight, parallel light beam (e.g., laser light). The impact of a microparticle in the interactive area is detected by means of a photoelectric element, e.g., a quick-acting photodiode, with which a transmission change in the optical path length or scattered light measurement is executed.

Viewed from another aspect, a device according to the invention consists of a combination of the cited detector device with a signal processing circuit and locator, which interact with an adjustment device of a dispensing head. Such an arrangement is preferably used to calibrate the impact points of a group of dispensers in a dispensing head.

The advantage to the invention is that the impact points of a dispensing head or a corresponding microparticle placement device can be determined fully automatically, rapidly and reliably. The position is determined with a simple detector, avoiding conventional image recognition procedures. In addition to the high sensitivity during individual particle detection, the advantages to the invention also include noise immunity, speed, accuracy and the relatively low costs of the detector.

Additional advantages and particulars of the invention are described below making reference to the drawings, which show.

In the following, the invention shall be explained based on a horizontally manipulable dispensing head with a linear dispenser device, e.g., formed by a group of piezoelectric micropipettes, for applying microscopic droplets on a substrate. However, the invention is not limited to such a micropipette device with vertical drop motion, but rather can be used in all types of microparticle placement devices, which can also carry two-dimensional dispenser devices or be equipped with horizontal motion components for moving the particles. Hence, a microparticle is a fluid drop or solid body with a characteristic size, which extends into the sub-millimeter range (up to the wavelength of visible light). The invention shall also be described with reference to the configuration of the detector device as an electro-acoustic sensor. The corresponding procedural steps of calibration, impact point determination, dispensing head positioning, signal evaluation, etc. can be used in a similar fashion in the case of an electro-optical sensor, however.

Figure 1:
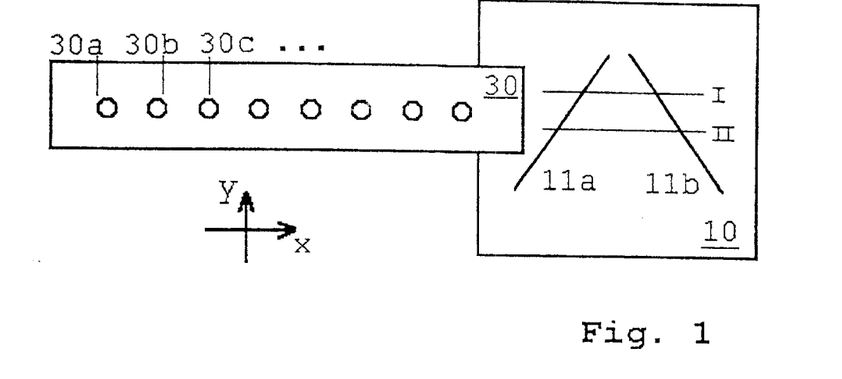
FIG. 1 a schematic top view of a dispensing head and a detector device to illustrate the procedure according to the invention.

FIG. 1 provides a diagrammatic top view of the relative alignment of a dispensing head 30 and a detector device 10. The dispensing head 30 can be moved in the x and y directions in the plane of projection. The x and y directions span a plane parallel to the target plane defined by detector wires 11a, 11b. To execute the following procedural steps, the dispensing head 30 is repeatedly moved along at least two straight, parallel, spaced-apart traversing paths I and II, whose vertical projections on the target plane intersect the detector wires 11a, 11b, moving over the detector device. The dispensing head is actuated with an adjustment device (see below), which is connected with a locator (see below). The locator provides coordinates in an environmental coordinate system, which constitutes the reference for all locations specified in the following. These encompass the current dispensing head coordinates, which are equated with the coordinates of a reference dispenser (e.g., dispenser 30a) for simplification purposes. The coordinates of the remaining dispensers (measuring dispensers 30b, 30c, ... ) arise from the dispersing head coordinates and respectively known, measurable coordinates of the measuring dispensers relative to the reference dispenser.

The reference dispenser coordinates (the dispensing head coordinates) are first determined for the dispensing head positions at which a microdrop originating from the reference dispenser hits one of the detector wires 11a, 11b. At least four impact points on detector wires are required for the subsequent measuring dispenser coordinate evaluation, which correspond to the four points of intersection between the projections of traversing paths I, II and the detector wires 11a, 11b. To ascertain the reference dispenser coordinates, the dispensing head is first aligned on traversing path I, and moved over the detector device on this path. The detector wires 11a, 11b are traversed at a constant traveling speed and drop emission rate. The traveling speed, frequency, drop diameter and dispenser-wire distance are selected as a function of the respective application and appropriate to the dimensions of the detector device. In particular, the frequency in relation to the traveling speed is selected in such a way that the realized number of drops per length unit is significantly lower than the position resolution of the adjustment device for the dispensing head. For example, the traveling rate of the dispensing head measures roughly 2.5 mm/s, the drop emission rate or frequency roughly 500 drops per second, the drop diameter roughly 50 to 60 pm, and the dispenser-wire distance roughly 2–3 mm for a detector device with detector wires having a length of roughly 3 cm and a distance ranging from roughly 1.5 to 3 cm. When traversing over the first detector wire 11a corresponding to position $P_1$ (see FIG. 2), the latter is hit by the microdrop. Already the first strip of a microdrop deflects the detector wire and (as described below) generates a detector signal on which the current reference dispenser coordinates are stored. Storing is accompanied by a check of whether a spurious signal was present. If this is the case, the detector signal is discarded. After the first detector wire 11a is hit at P$_1$, the dispensing head 30 is moved on to the second detector wire 11b for determining the reference dispenser coordinates according to point P$_2$. The same sequence of events subsequently runs its course along the parallel, spaced-apart traversing path II. The distance selected between the traversing paths I and II must be suited to achieve a sufficient measuring accuracy, and can measure roughly 1 to 3 cm, for example.

As soon as the reference dispenser coordinates have been determined based on impact points P$_1$ to P$_4$, the impact points of microdrops from each of the remaining measuring pipettes 30b, 30c, . . . are determined. To this end, the dispensing head 30 is moved along one of traversing paths I, II or, if the detector wires are expected to become contaminated along these traversing paths after the first calibration steps depending on the substance, along a third, parallel traversing path over the detector device 10. To determine the impact points of each measuring dispenser, the detector device can be traversed repeatedly based on the number of measuring dispensers, with microdrops being dispensed from one of the measuring dispensers. As an alternative, however, the dispensing head can be passed over the detector device only once, and a sequence of drops can be consecutively dispensed from only one of the measuring dispensers, when the latter is located over one of the detector wires. To prevent signal errors stemming from detector wire contamination, the repeated or single traversing of the detector device can be accompanied by a simultaneous displacement of the dispensing head vertically to the traveling direction, so that the detector wire is hit by a microdrop at another location. The impact points of microdrops from measuring dispensers will be designated Q$_1$, Q$_2$ below.

Figure 2:
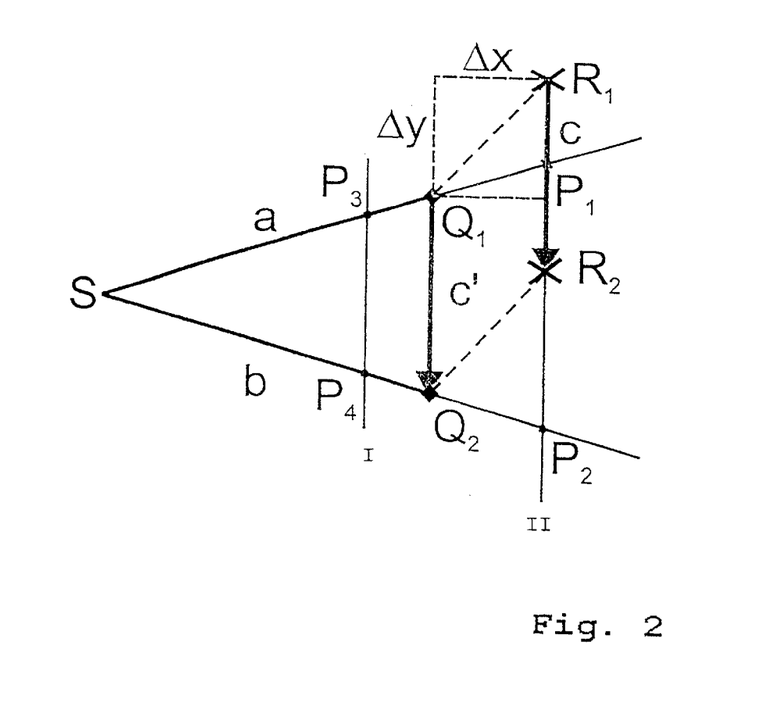
FIG. 2 a geometric representation to illustrate the evaluation diagram according to the invention.

The impact points Q$_1$, Q$_2$ the microdrops from the measuring dispensers are calculated as follows based on the reference dispenser coordinates corresponding to reference impact points P$_1$ to P$_4$ and by measuring the known measuring dispenser coordinates R$_1$, R$_2$ (see FIG. 2).

The line equations of the detector wires are first determined from the reference dispenser coordinates for the reference impact points P$_1$, P$_3$ or P$_2$, P$_4$. The coordinates of the (imaginary) point of intersection S between the two detector wires are then determined from the line equations. Paths |SQ$_1$| and |SQ$_2$| arise from the set of beams as follows:

$$|SQ_1|=(|Q_1Q_2|\cdot|SP_1|)/|P_1P_2|$$

$$|SQ_2|=(|Q_1Q_2|\cdot|SP_1|)/|P_1P_2|$$

Since the measuring dispenser coordinates R$_1$, R$_2$ at which the respective measuring dispensers are located at the time of microdrop impact are known, and the paths |Q$_1$Q$_2$| and |R$_1$R$_2$| are the same, |Q$_1$Q$_2$| can be substituted by |R$_1$R$_2$| in the equations. As a result, the sums of the vectors respectively leading from S to Q$_1$ or Q$_2$ are known. Since their direction in turn matches the vectors leading from S to P$_1$ or P$_2$, only the ratio |SQ$_1$|/|SP$_1$| or |SQ$_1$|/|SP$_1$| which measures |R$_1$R$_2$|/|P$_1$P$_2$| in both cases, need still be taken into account to determine the coordinates of points Q$_1$, Q$_2$.

The coordinates of points Q$_1$, Q$_2$ determined in this way relate to the aforementioned coordinate system of the locator. The deviation of these coordinates $\Delta x$, $\Delta y$ from the coordinates of the measuring dispenser R$_1$, R$_2$ represents the desired deviation of the impact point from the position of the measuring dispenser. These deviation coordinates can be used within the framework of a dispensing head calibration to ascertain the impact points of each dispenser of a dispensing head in a reproducible manner, or to correct the position of a dispensing head during operation to realize a specific dispensing position relative to a desired substrate impact point.

In the following, details of the detector device 10 according to the invention will be described making reference to FIG. 3 and 4.

Figure 3:
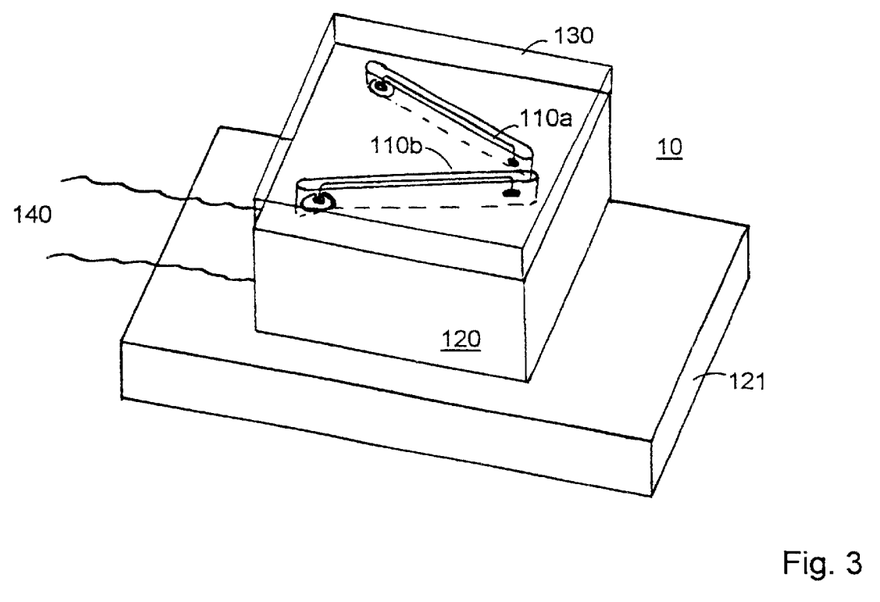
FIG. 3 a perspective view of a detector device according to the invention.

In FIG. 3, the detector device 10 comprises two detector sections 110a, 110b, which are secured to a carrier block 120. The carrier block 120 also carries a protective cover 130, which covers the top side of carrier block 120, except for detector sections 110a, 110b. Instead of the protective cover 130, which leaves detector sections 110a, 110b bare, recesses can be introduced (milled) on the top side of the carrier block 120 to accommodate parts of the detector sections 110a, 110b. This protects the detector wires against mechanical influences and provides a sound screen against interference. The detector sections 110a, 110b each have a microphone (see FIG. 4) that is connected with the signal processing circuit 200 (see FIG. 5) via connecting lines 140. The carrier block 120 and protective cover 130 preferably consist of a massive plastic material (e.g., PMMA). The height of the carrier block 120 (with carrier plate 121, if necessary) can be selected in such a way that the height of the detector sections 110a, 110b corresponds roughly to the height of a substrate to be coated relative to a dispensing head to be examined. As an alternative, the distance of the dispensing head from the detector sections 110a, 110b (z direction) can be ascertained when using the detector device with any height, and to consider this distance during later operation of the dispensing head when adjusting the height over a substrate.

Figure 4:
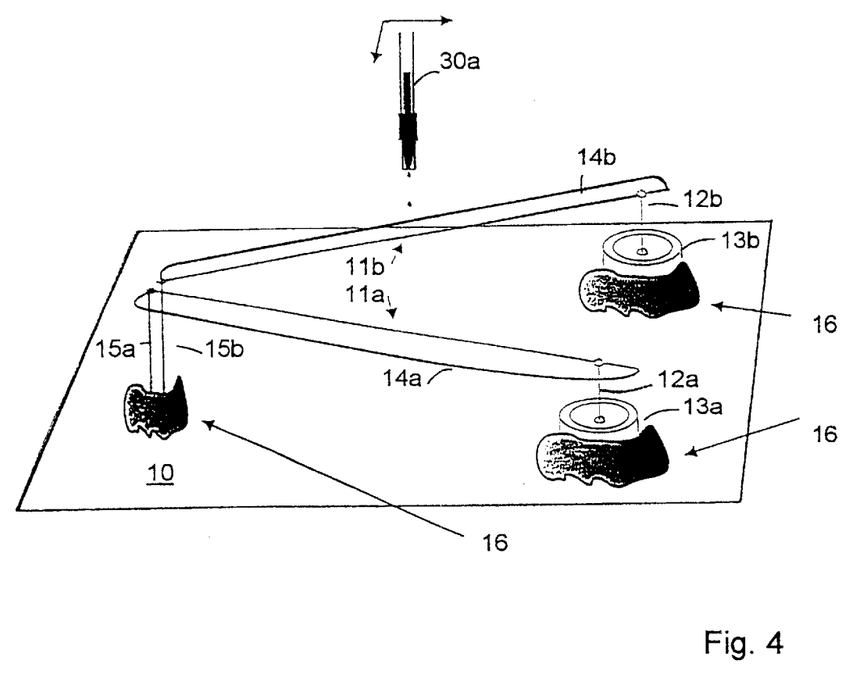
FIG. 4 a perspective view of particulars of a detector device according to FIG. 3.

FIG. 4 shows details of the detector sections 110a, 110b (without the carrier block and protective cover). The detector sections 110a, 110b each comprise a detector wire (or drop catching wire) 11a, 11b, which is oscillation-coupled with a microphone 13a, 13b. Each detector wire 11a, 11b is aligned straight. To this end, a fastening device 14a, 15a, 14b, 15b is provided that consists of a clamp clip 14a, 14b and a carrier element 15a, 15b. Each clamp clip 14a, 14b is aligned by the respective carrier element 15a, 15b in such a way that the fixed detector wires 11a, 11b form a predetermined angle to each other (preferably <90°, e.g., roughly 45°), and thereby fix a detector target plane. During use, the detector target plane is parallel to the x-y plane of the adjustment device (not shown) of a dispensing head with the dispenser 30a.

The ends of the detector wires 11a, 11b are each fixed at the ends of clamp clips 14a, 14b. A pretensioning takes place in which each detector wire is stretched in the expected application temperature range to the point that it runs straight between the clamp clip ends. Each detector wire forms an interactive area mentioned above. The in this case linear shape of the interactive area gives it a straight limitation on all sides. However, it is also conceivable to use an oscillating membrane as the oscillating element, which must exhibit a straight limitation relative to the formation of the impacting sequence of drops to realize the evaluation principle outlined above.

The detector wires 11a, 11b consist of an elastic, oscillatory material. They are preferably wires made out of metals with a high sound conductance, e.g., copper, so that positioning the microphone relative to the detector wire is not problematical. In the example shown, the microphone coupling element 12a, 12b is located near the respective detector filament end, but at a distance from the clamp clip end. Each detector coupling element 12a, 12b is connected with the respective microphone, preferably with the respective microphone membrane. The detector wires 11*a*, 11*b* have a diameter of roughly 40 μm. In general, the diameter of each detector wire is selected in such a way that the sound attenuation is sufficiently low on the one hand, and the wire stability is sufficiently high on the other. The mechanical oscillation in each wire is attenuated, but at a low enough level that the oscillation can be detected in a sufficiently reproducible manner during subsequent signal processing. If the wire is too thin, there is a danger of tearing during the impact of microparticles in the detection process. The clamp clip diameters measure roughly 0.9 mm.

The elements of detector sections 110*a*, 110*b* are connected with the carrier block 120 via sound-attenuating mounts (see FIG. 3). The sound-attenuating mounts consist of foam padding 16 or comparable attenuating devices, for example. A shared mount is provided for carrier elements 15*a*, 15*b*. It is possible to secure both clamp clips 14*a*, 14*b* on a shared carrier element.

Figure 5:
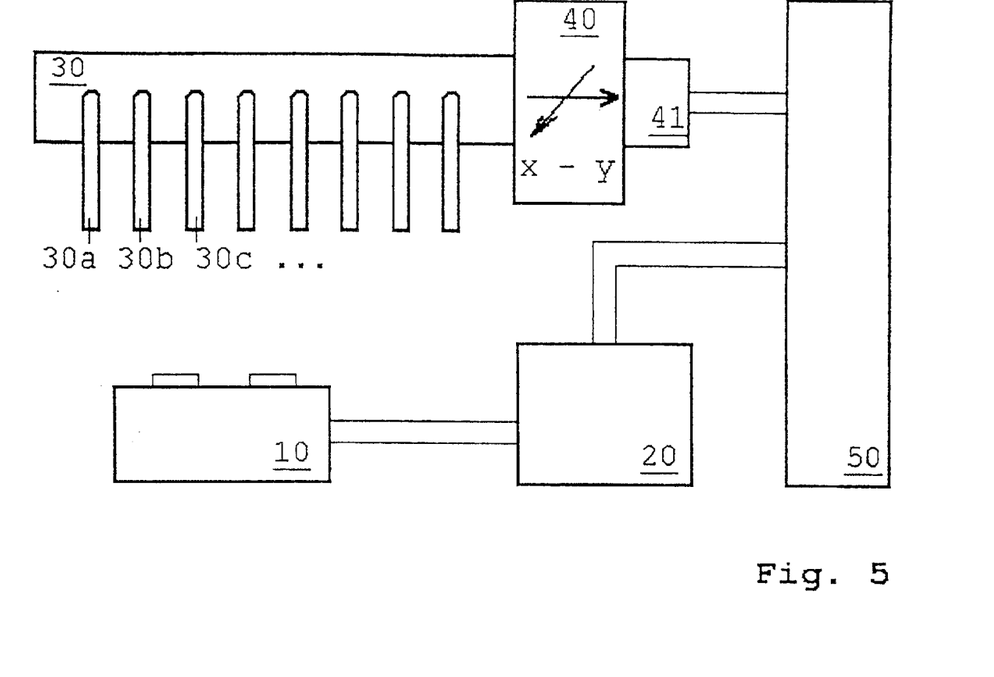
FIG. 5 a schematic block diagram of a combination according to the invention of the detector device with the adjustment device of a dispensing head.

FIG. 5 presents a diagrammatic view of the combination of the described detector device 10 with a dispensing head 30 to form a calibration device for the dispensing head. The detector device 10 is connected with a signal processing circuit 20, which is set up to derive digital control signals from the detector signals of the detector device 10, and whose particulars are described below drawing reference to FIG. 6. The digital control signals are relayed to a controller 50, e.g., a computer with two digital inputs and a digital output. The controller 50 delivers signals to the (x-y-z) adjustment device 40 with locator 41, with which the dispensing head 40 can be moved in a z-direction in the x-y plane, parallel to the detector target plane and vertical thereto. The dispensing head 30 consists, for example, of numerous sequentially arranged pipettes 30*a*, 30*b*, 30*c* . . . , which are filled with various substances when used for the intended purpose.

Figure 6:
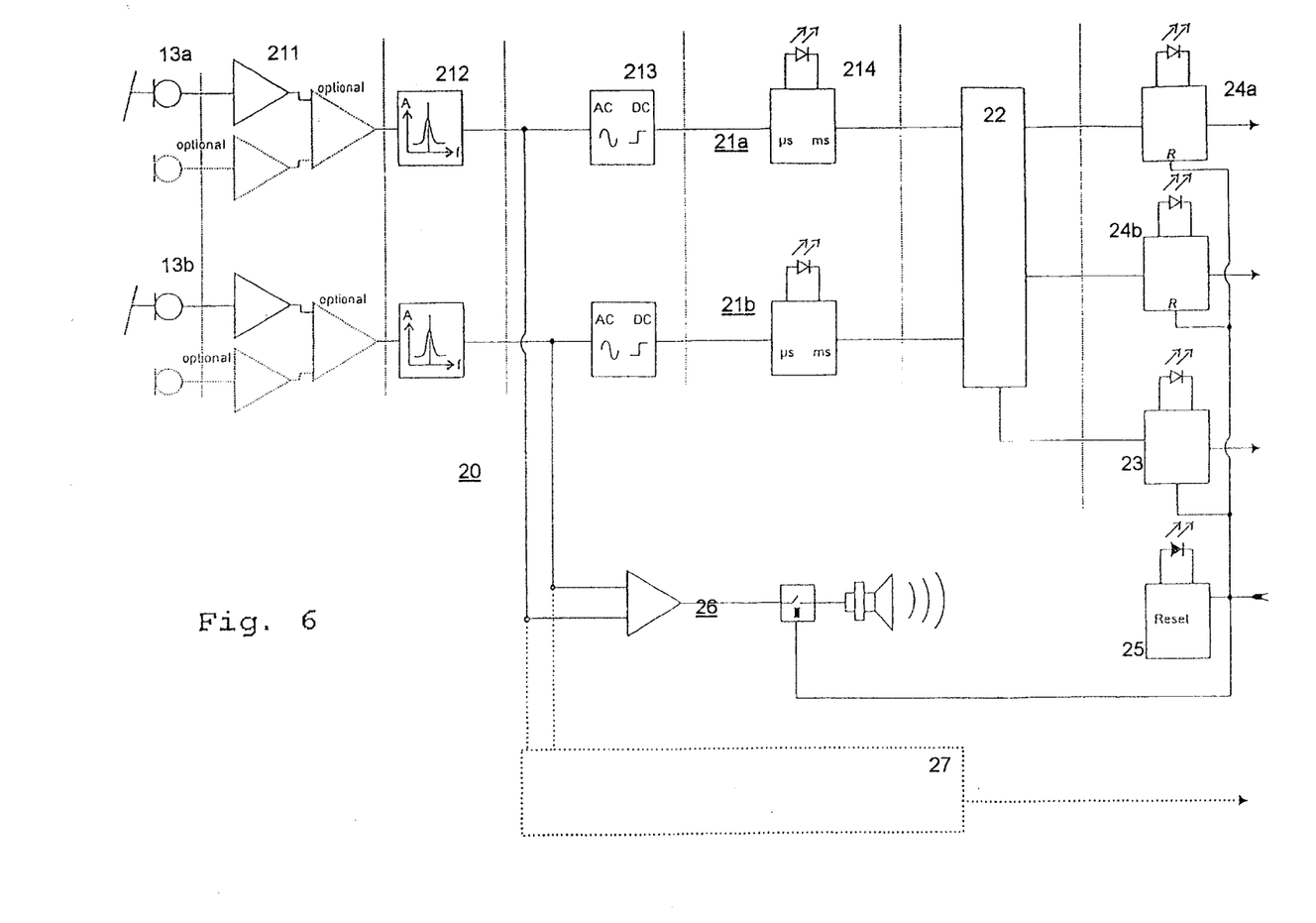
FIG. 6 a block diagram of a signal processing circuit from FIG. 5.
Figure 7A:
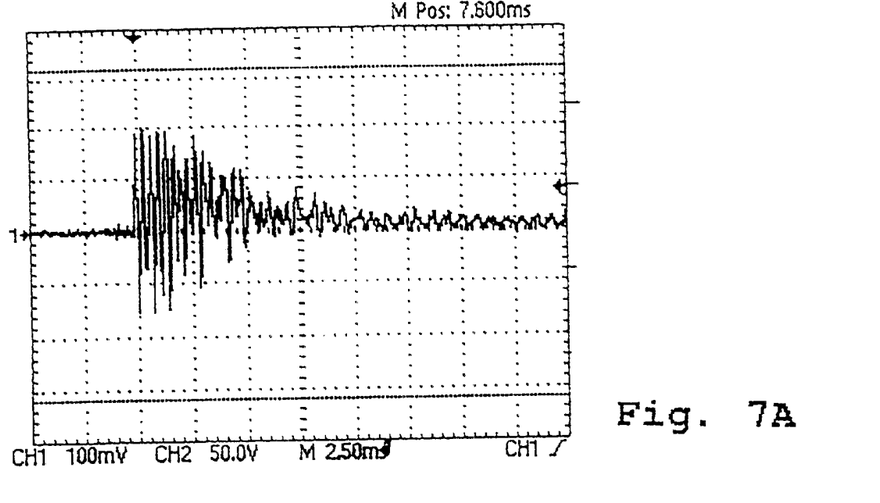
FIGS. 7A, B curves illustrating the signal progressions of the detector device, and FIG. 8 a diagrammatic view of the deviation between relative dispenser coordinates and relative impact point coordinates.
Figure 7B:
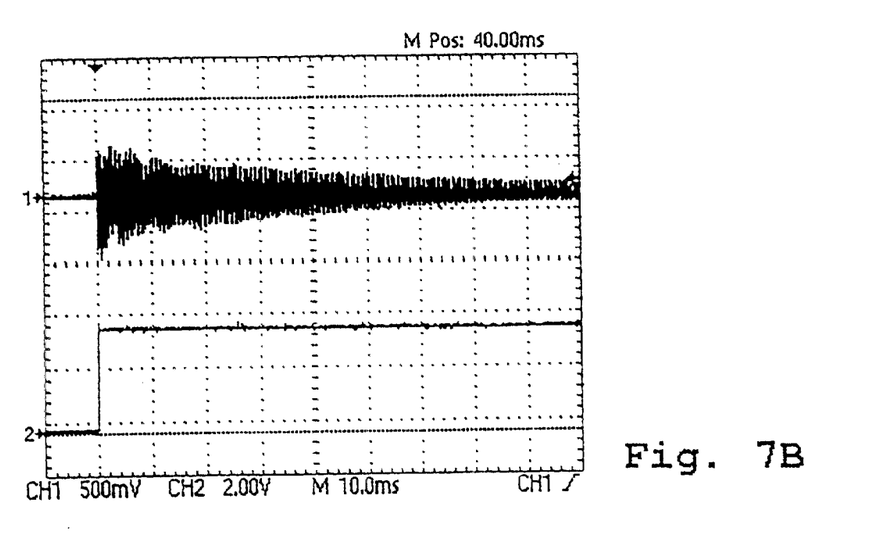

For each of the signal converters (e.g., microphones 13*a*, 13*b*) of the detector device in FIG. 6, the signal processing circuit 20 consists of a digital signal channel 21*a*, 21*b*, and a logic circuit 22, an error display 23, hit signal circuits 24*a*, 24*b*, a reset circuit 25 and an audio device 26. In addition, a sound detection circuit 27 (e.g., RSC-164 from Sensory Inc., USA) can be provided, which is set up for purposes of additional monitoring during signal evaluation by providing a signal when a drop noise is detected. The digital signal channel 21*a* (and correspondingly, the second digital signal channel 21*b*) consists of a preamplifier 211, a band pass 212, a rectifier 213 and an extension circuit 213. The preamplifier 211 is used to preliminarily amplify the detector signal from the microphone 13*a*. The expected drop frequency spectrum is filtered out at the band pass 212. As evident from FIG. 7*a*, an oscillating detector wire exhibits a characteristic spectrum after hit by a microdrop, whose frequency focal point lies at roughly 3.5 kHz, and to which the band pass 212 is tuned. After the band pass, the filtered detector signal has the curve progression shown in FIG. 7*b* (top curve). The filtered detector signal is rectified at the rectifier 213 to generate a signal with TTL level (TTL pulse). The rectified signal has the curve progression shown in FIG. 7*b* (bottom curve). At the extension circuit 214, the TTL pulse is converted from the ps to ms range. A light-emitting diode indicates the presence of the extended pulse.

The logic circuit 22 is provided for precluding error signals. If TTL pulses are triggered simultaneously at the digital signal channels 21*a*, 21*b*, it means that the detector signal was not generated by the impact of a drop, but by a malfunction that affected both detector wires at the same time. In this case, the event is indicated on the error display 23, which relays a spurious signal to the controller 50 (see FIG. 5). If a TTL pulse is present at the channel 21*a* or channel 21*b* during drop detection, the corresponding signal is relayed to one of the hit signal circuits 24*a*, 24*b*, which each indicate whether the first or second detector wire was hit by means of a light-emitting diode. In turn, the hit signal circuits 24*a*, 24*b* are used to extend the display time, so as to enable visual observation by the user. The digital signals from the hit signal circuits are each relayed to the controller 50, which is connected with the axis control system (controller 40, locator 41, see FIG. 5).

The signal processing circuit 20 also comprises the reset circuit 25, which can be reset with a control signal at the beginning of the measurement (e.g., to "high" or "active"), and receives a reset signal following a correct signal acquisition by the controller 50. This signal is also relayed to the hit signal circuits 24*a*, 24*b*.

The audio device 26 is used to make the drop noise audible. It consists of a LF amplifier with downstream loudspeaker, which responds based on the state of a reset switch connected with the reset circuit 25.

In addition to the interference suppression function of the logic circuit 22, each digital signal channel can, according to the invention, be provided with an add-on sound converter 215 and a preamplifier 216, whose output signal along with the output signal of the preamplifier 211 is subjected to differential amplification at the differential amplifier 217, whose output signal is present at the band pass 212. These add-on circuit components are preferably provided in an environment with a high interference level during operation of the detector device. The interference level is continuously recorded with an add-on microphone, and compared by the differential amplifier with the useful signal from the microphone 13*a* of the detector.

As a rule, only one rapid and low-delay acquisition of the drop impact, and hence the leading edge of each TTL pulse, is of interest for the subsequent acquisition of current coordinates of the locator 41 (see FIG. 5). In general, only that signal in the drop sequence is evaluated which triggers the first drop in the signal processing circuit that impacts the respective detector wire or exceeds the limit of the interactive area. This applies in particular to cases where the microdrop is larger than the diameters of the detector wires. The subsequent drops are precluded from detection via the suitable selection of the reset signal.

In addition to processing digital signals from the signal processing circuit 20, the controller 50 is set up to calculate the deviation coordinates as explained above, and to provide correction signals to the locator 41 during use of the dispensing head 30 for the intended function to charge a substrate. These correction signals preferably make it possible to manipulate the dispensing head 30 in such a way that microdrops can be fired at a predetermined substrate position from each of the micropipettes 30*a*, 30*b*, 30*c*, . . . with a high precision (error<10 . . . 20 μm). As a result, the locational accuracy of microparticle placement becomes independent of any arising misalignments of the individual dispensers, and now depends solely on the accuracy of the position setting of the adjustment device.

The signal processing circuit 20 according to FIG. 6 can additionally be provided with a signal evaluation circuit (not shown), which is set up to determine the drop velocity from the detector signals. In general, the velocity of microparticles is determined based on one of the following procedures. In a first scenario, a detector section of the detector device is subjected to multiple bombardments with the same x-y dispensing head position, but from different heights (z-direction) relative to the respective detector section. Depending on the height, the TTL signal characteristic for the hit arises at different times. The velocity is calculated from the time differentials of the impact times and corresponding height differences assuming an acceleration-free motion. As an alternative, when using piezoelectric micropipettes, a trigger pulse for the piezoelectric sensor can be used as the starting pulse, and the impact TTL signal can be used as the end pulse for a time measurement, wherein the velocity is again determined from the ratio between the measurable distance covered to the measured start-end time. Finally, it is also possible to derive the start pulse from the respective sound converter in an electro-acoustic detector device. For example, if the means for electromagnetic screening are removed in a microphone, the microphone will respond to an electromagnetic pulse radiated by the piezoelectric sensor when the trigger pulse is present.

What is claimed is:

1. A procedure for detecting microparticles moving from dispensers of a dispensing head to a target, with the steps:

moving said dispensing head while depositing a sequence of microparticles from a reference dispenser over a detector device on a carrier with two linear bound, electro-acoustic or electro-optic interactive areas, which fix a target plane, along at least two, straight parallel traversing paths, determining the reference dispenser coordinates for the dispensing head positions, in which microparticles impact said interactive areas, moving the dispensing head while depositing a sequence of microparticles from at least one measuring dispenser parallel to said traversing paths, and determining impact point coordinates for said dispensing head positions in which microparticles impact said interactive areas from said measuring dispenser.

2. A procedure according to claim 1, in which correction signals are determined from the deviation coordinates for a locator of said dispensing head for adjusting said dispensers to move said microparticles on predetermined substrate positions.

3. A procedure according to claim 2, in which said dispenser coordinates of said dispensing head are calibrated based on said deviation coordinates.

4. A procedure according to claim 1, in which said impact of a said microparticle on one of said interactive areas is detected by acquiring a detector signal, that is converted into a signal, whose leading edge is characteristic for the time of impact of said microparticle.

5. A procedure according to claim 1, in which the deviation coordinates between said coordinates of measuring dispensers and said impact point coordinates are determined from the coordinates of said dispensing head, relative coordinates of said measuring dispensers at said dispensing head and said impact point coordinates.

6. A detector device for detecting the impact points of microparticles, which are emitted by several dispensers of a dispenser row, with two linear bound, electro-acoustic or electro-optic interactive areas, which are arranged at a predetermined angle to each other and fix a target plane, wherein each interactive area is set up to emit a detector signal when a microparticle hits the interactive area.

7. A detector device according to claim 6, in which each of said interactive areas exhibits an electro-acoustic detector section with an oscillating element that is oscillation-coupled with a sound converter.

8. A detector device according to claim 7, in which said oscillating element is a detector wire and said sound converter is a microphone.

9. A detector device according to claim 6, in which each of said interactive areas exhibits an electro-optic detector section, which is intersected by a straight, parallel light beam, and has at least one photo element.

* * * * *

UNITED STATES PATENT AND TRADEMARK OFFICE
CERTIFICATE OF CORRECTION

PATENT NO. : 6,467,328 B1
DATED : October 22, 2002
INVENTOR(S) : Kalkum et al.

It is certified that error appears in the above-identified patent and that said Letters Patent is hereby corrected as shown below:

<u>Title page,</u>
The title page showing an illustrated figure, should be deleted and substituted therefor the attached title page.

<u>Drawings,</u>
Delete drawing sheets 1 and 5, and substitute therefor the drawing sheets, consisting of drawing Figs. 1 and 6, as shown on the attached sheets.

Signed and Sealed this

Eighth Day of April, 2003

JAMES E. ROGAN
*Director of the United States Patent and Trademark Office*

United States Patent
Kalkum et al.

(10) Patent No.: US 6,467,328 B1
(45) Date of Patent: Oct. 22, 2002

(54) PROCESS AND DEVICE FOR DETECTING MICROPARTICLE MOVEMENT

(75) Inventors: Markus Kalkum, New York, NY (US); Markus Kietzmann, Wolfratshausen (DE); Martin Müller, Berlin (DE)

(73) Assignee: Max-Planck-Gesellschaft zur Forderung der Wissenschaften e.V. (DE)

(*) Notice: Subject to any disclaimer, the term of this patent is extended or adjusted under 35 U.S.C. 154(b) by 0 days.

(21) Appl. No.: 09/555,068

(22) PCT Filed: Nov. 23, 1998

(86) PCT No.: PCT/EP98/07558
§ 371 (c)(1),
(2), (4) Date: Jul. 24, 2000

(87) PCT Pub. No.: WO99/27372
PCT Pub. Date: Jun. 3, 1999

(30) Foreign Application Priority Data

Nov. 24, 1997 (DE) .......................... 197 52 010

(51) Int. Cl.[7] ............................ G01N 1/00
(52) U.S. Cl. ............................. 73/1.01
(58) Field of Search ................. 73/1.01, 1.79, 73/1.81, 865.5, 488; 356/614, 27, 28; 324/178; 222/32, 41

(56) References Cited

U.S. PATENT DOCUMENTS 5,508,200 A    4/1996   Tiffany et al.

FOREIGN PATENT DOCUMENTS

| CH | 668 130 A5 | 11/1988 |
|----|-----------|---------|
| EP | 0 601 213 | 10/1992 |
| EP | 0 775 587 A1 | 4/1996 |

OTHER PUBLICATIONS

Patent Abstracts of Japan—Detecting Device for Speed of Ink Particles in Ink Jet—Jan. 31, 1981, vol. 5/No. 17.
Analytical Chemistry, vol. 69, Feb. 15, 1997—Characterization of an Inkjet Chemical Microdispenser for Combinatorial Library Synthesis.

Primary Examiner—Robert Raevis
(74) Attorney, Agent, or Firm—Cook, Alex, McFarron, Manzo, Cummings & Mehler, Ltd.

(57) ABSTRACT

For the detection of the position and/or velocity of microparticles which move from dispensers of a dispensing head (30) to a target, a detector target with two linear bound, electro-acoustic or electro-optic interactive areas which fix a target plane is used. When microparticles impact on the interactive areas, detector signals are determined from which along with the dispensing head position motion parameters of the microparticles are obtained.

9 Claims, 6 Drawing Sheets